United States Patent

Dageforde

[11] Patent Number: 5,804,695
[45] Date of Patent: Sep. 8, 1998

[54] GAS DIVIDING METHOD AND APPARATUS

[75] Inventor: Allen F. Dageforde, Orange, Calif.

[73] Assignee: Horiba Instruments Incorporated, Irvine, Calif.

[21] Appl. No.: 856,048

[22] Filed: May 14, 1997

Related U.S. Application Data

[63] Continuation of Ser. No. 598,633, Feb. 12, 1996, abandoned, which is a continuation of Ser. No. 146,962, Nov. 2, 1993, abandoned.

[51] Int. Cl.[6] .................................................. G01N 31/00
[52] U.S. Cl. ............................................................ 73/1.07
[58] Field of Search ................... 73/1 G, 1.07; 137/602, 137/896, 606, 607

[56] References Cited

U.S. PATENT DOCUMENTS

| | | | |
|---|---|---|---|
| 4,254,797 | 3/1981 | Mayeaux | 73/1 G |
| 4,498,496 | 2/1985 | Barcellona et al. | 73/1 G |
| 4,555,930 | 12/1985 | Leach et al. | 73/1 G |
| 4,852,384 | 8/1989 | Woolbert et al. | 73/1 G |
| 4,977,776 | 12/1990 | Shindo et al. | 73/1 G |
| 5,157,957 | 10/1992 | Mettes et al. | 73/1 G |

OTHER PUBLICATIONS

Horiba Instruments Incorporated, Instruction Manual for SGD—710, Jul. 1986.
Horiba Instruments Incorporated, Instruction Manual for SGD—A10, Nov. 1988.
Horiba Instruments Incorporated, Standard Gas Dividers SGD Series, 1988.
Enrivonics Inc., Series 2000 Computerized Multi–Component Gas Mixer, Owner's Manual 1991.

*Primary Examiner*—Robert Raevis
*Attorney, Agent, or Firm*—Brooks & Kushman P.C.

[57] ABSTRACT

A gas dividing and blending system including a gas divider for generating a mid-span gas for more than one analyzer at the same time so that the analyzers can run their mid-span checks at the same time. A mid-span gas is generated using the span gases for the analyzers. If desired, a separate diluent gas may also be mixed with the span gases to generate a mid-span gas. Once a mid-span gas is generated, it is then simultaneously delivered to each analyzer which uses the mid-span gas to perform its mid-span gas check at the same time as the other analyzers.

16 Claims, 2 Drawing Sheets

GAS DIVIDING METHOD AND APPARATUS

This is a continuation of application Ser. No. 08/598,633 filed on Feb. 12, 1996, now abandoned, which is a continuation of Ser. No. 08/146,962 filed Nov. 2, 1993, now abandoned.

TECHNICAL FIELD

This invention relates to a method and apparatus for dividing gases, and more particularly to a gas blending system wherein the mid-span gases are generated for two or more gas analyzers simultaneously by blending the span gases with each other to provide a repeatable mixture of gases having the desired mid-span concentrations.

BACKGROUND OF THE INVENTION

Gas analyzers are frequently used to determine the concentration of a particular component, such as hydrocarbons (HC), $NO_X$, CO, $CO_2$, etc. in a gas sample. To ensure accuracy and reliability, a gas analyzer must be properly calibrated. The proper operation of a gas analyzer requires that, in addition to the zero and span check, a mid-span check be run by introducing a mid-span gas to confirm that the linearity or degree of non-linearity of the analyzer has not changed significantly from the calibration curve stored in the computer which calculates component concentration from the analyzer output. A mid-span gas has less than 100% of full scale concentration, and for certain analyzers, a mid-span gas is defined as a gas having 10 to 20% of full scale concentration.

With the current technology, a mid-span gas is generated by blending a diluent gas with a span or mixture gas in various proportions using capillary flow control. The generated mid-span gas is then delivered to an analyzer to perform the mid-span calibration check. Gas dividers can generate any of a number of different concentrations required for the calibration of an analyzer employing this flow rate ratio mixing method. With this method, the flow rates of a span gas or mixture of span gases, and a diluent gas are controlled by capillary tubes and the concentration of the mid-span gas generated is determined by the ratios of those flow rates. The concentration of the generated mid-span gas is changed by selecting the number of capillary tubes in which a span gas or mixture of span gases and a diluent gas flow, respectively. All capillaries in the system have gas flow, either a span gas, mixture of span gases or a diluent gas so the more capillaries which have mixture/span gas flow, the greater the concentration of the generated mid-span gas.

SUMMARY OF THE INVENTION

The present invention provides a single apparatus which may be connected to a plurality of analyzers to generate the mid-span gas for each of those analyzers at the same time, with or without a separate diluent gas, allowing the mid-span calibration checks for all of the analyzers to be run at the same time. This is accomplished by using the span gases for the other analyzers as diluents for the span gas of a given analyzer. A separate diluent may also be mixed with the span gases if desired.

It is, therefore, an object of this invention to provide a gas divider and method of dividing gases which generates the mid-span gases for two or more analyzers simultaneously to provide a repeatable mixture of gases having the desired mid-span concentrations for the calibration of the analyzers.

It is another object of this invention to provide a gas divider and a method of dividing gases which generates the mid-span gases for two or more analyzers simultaneously to allow all of the analyzers to run the mid-span calibration check at the same time.

This invention is adapted to be embodied in a gas dividing and blending system including a gas divider for generating a mid-span gas for a plurality of analyzers simultaneously using the span gases for the analyzers. The gas divider comprises a plurality of span gas inlets each adapted to receive a span gas, a plurality of span gas inlet lines each in communication with a respective one of the plurality of span gas inlets, a plurality of flow controlling means each coupled to a respective one of the plurality of span gas inlet lines, a gas conduit for blending the span gases to generate a mid-span gas, and means for supplying the generated mid-span gas to each of the plurality of analyzers.

Another feature of the invention is adapted to be embodied in a method of blending gases for generating a mid-span gas for a plurality of analyzers simultaneously using the span gases for the analyzers, comprising the steps of supplying at least two span gases to a gas divider, controlling the flow of each of the two span gases, blending at least two span gases to generate a mid-span gas, and supplying the mid-span gas to a plurality of analyzers simultaneously.

DETAILED DESCRIPTION OF THE PREFERRED EMBODIMENTS

Figure 1:
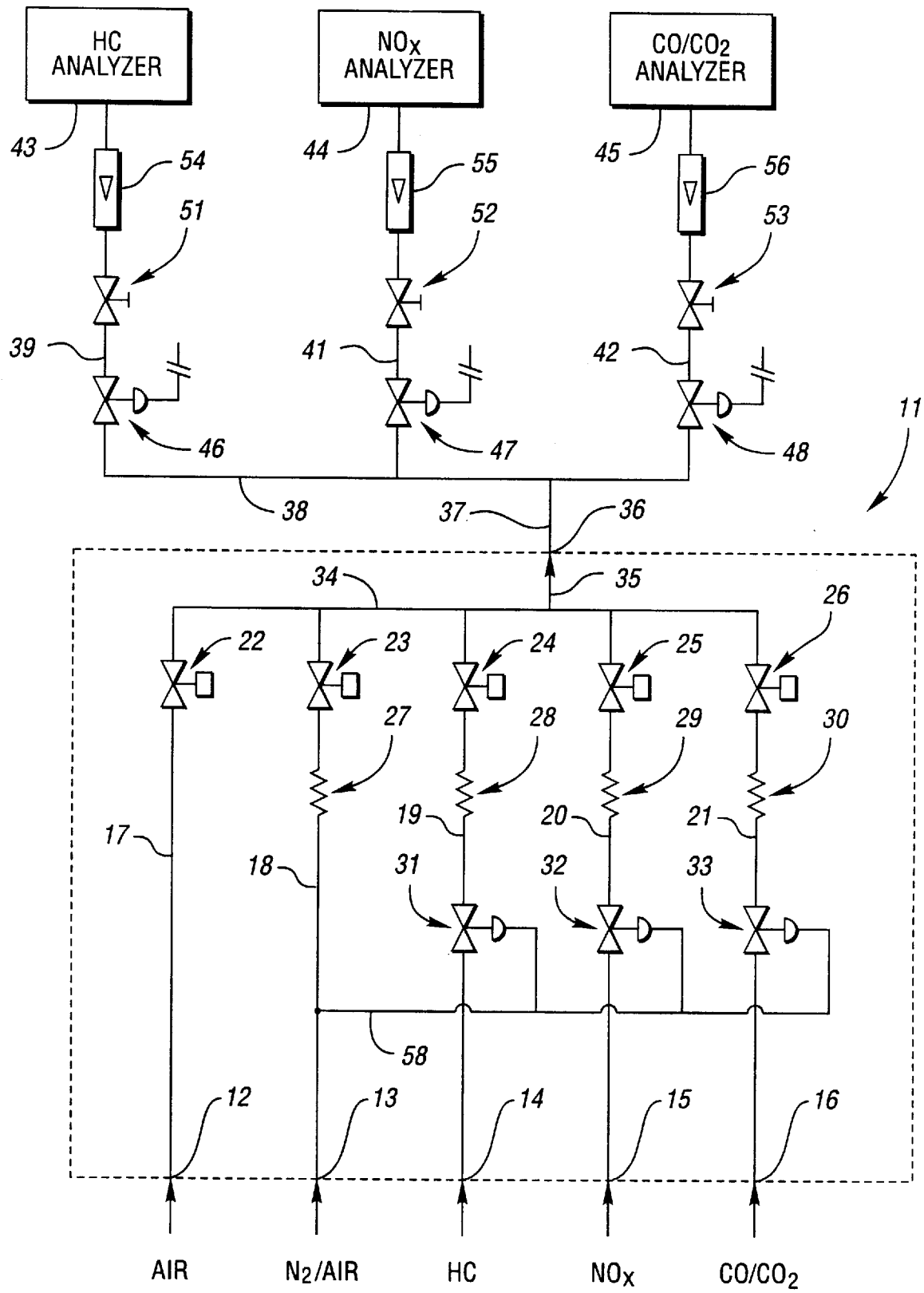
FIG. 1 is a schematic illustration of a gas dividing and blending system constructed in accordance with embodiments of the invention and showing a gas divider connected to a plurality of gas analyzers for generating a mid-span gas to be used by each of these analyzers in running its mid-span check simultaneously.

Referring to FIG. 1, a gas divider for generating mid-span gases is shown schematically and is identified generally by the reference numeral 11. The gas divider 11 has a plurality of inlets, each adapted to be coupled to a gas supply by means of an appropriate connector. In FIG. 1, the gas divider has five (5) inlets: an air inlet 12, a diluent gas inlet 13 which may be $N_2$ or air, a hydrocarbon (HC) gas inlet 14, an $NO_X$ gas inlet 15 and a CO or $CO_2$ gas inlet 16. Although a separate diluent gas inlet 13 is provided, it should be noted that the mid-span gases may be generated with or without using air or $N_2$ as a diluent gas and instead mixing the span gases (HC, $NO_X$, CO and/or $CO_2$) only with each other.

It will be seen that each inlet 12 through 16 leads to a corresponding inlet gas line 17 through 21 respectively. Each gas is introduced into its respective inlet 12 through 16 under pressure. The span gases are typically individually stored in bottles with pressure regulators and are introduced into their inlets at a pressure of approximately thirty pounds per square inch. The separate diluent gas is also stored in a bottle having a pressure regulator. If used, the separate diluent is usually introduced into its inlet at a pressure of approximately twenty pounds per square inch. Each inlet gas line 17 through 21 has coupled to it a solenoid valve 22 through 26 respectively for opening and closing its corresponding inlet gas line.

Upstream of each of the solenoid valves 23 through 26 in each of the inlet lines 18 through 21 is a capillary tube 27 through 30 respectively for controlling the flow rate of the gas. Upstream of each capillary 28, 29 and 30 coupled to the corresponding inlet line 19 through 21 is a differential pressure controller 31, 32 and 33 respectively for creating a controlled pressure at the inlet to the capillaries for each span gas. The capillaries 27 through 30 and differential pressure controllers 31, 32 and 33 operate as hereinafter described. Downstream of the solenoid valves 22 through 26 is a gas conduit 34 which connects all of the inlet gas lines 17 through 21 with an outlet line 35 which terminates at an outlet 36.

The outlet 36 of the mid-span gas divider 11 is connected to a gas conduit 37 which is, in turn, connected to gas conduit or manifold 38 which connects with a plurality of gas lines 39, 41 and 42. As shown in FIG. 1, gas line 39 leads to an HC analyzer 43, gas line 41 leads to an $NO_X$ analyzer 44 and gas line 42 leads to a $CO/CO_2$ analyzer 45. Each gas line 39, 41 and 42 has coupled to it a spring loaded pressure controller 46, 47 and 48 respectively and a needle valve 51, 52 and 53 respectively. The spring loaded pressure controllers 46, 47 and 48 each vent to the atmosphere to provide a pressure drop of approximately three pounds per square inch. The adjustable needle valves 51, 52 and 53 are for individually adjusting the flow rate of the gas through the corresponding gas line to the corresponding analyzer. These individual flow rates are measured by the flow meters 54, 55 and 56 respectively which are downstream of the needle valves 51, 52 and 53 and coupled to the gas lines 39, 41 and 42 respectively.

A computer (not shown) is connected to the analyzers 43, 44 and 45 and is used for storing a response curve for each analyzer. These response curves are determined by procedures specified in the Federal Regulations and may be loaded into the computer utilizing software.

To check the response of each analyzer against the predetermined response curve for that analyzer, each analyzer must first be zeroed with either air or $N_2$. This check can be run simultaneously for each analyzer by introducing air through either inlet 12 or 13, or alternatively introducing $N_2$ through inlet 13. This "zeroing" check is done by opening either solenoid valve 22 or 23 and closing the rest of the solenoid valves in the inlet gas lines so that only air or $N_2$ flows through the gas divider 11. The needle valves 51, 52 and 53 are adjusted to provide the desired flow rate through the gas lines 39, 41 and 42 to each of the analyzers. The actual zero response of each analyzer 43, 44 and 45 is then compared with the appropriate predetermined response curve stored in the computer.

Once the analyzers 43, 44 and 45 are zeroed, the span or maximum response for each analyzer must be checked. To do this, one span gas at a time is introduced into the gas divider 11 and delivered to the appropriate analyzer. To run the span check for the HC analyzer 43, solenoid valves 22, 23, 25 and 26 are closed. Solenoid valve 24 is opened and HC gas is introduced through inlet 14, into the gas divider 11, and out the outlet 36 and to the HC analyzer 43. To run the span check for the $NO_X$ analyzer 44, only solenoid valve 25 is opened and the other solenoid valves 22, 23, 24 and 26 are closed. $NO_X$ span gas is then introduced through its inlet 15 and delivered to the $NO_X$ analyzer 44. To run the span check for the $CO/CO_2$ analyzers 45, only solenoid valve 26 is opened and the other solenoid valves 22 through 25 are closed. CO or $CO_2$ span gas is then introduced through its inlet 16 and delivered to the analyzer 45. After the span gas has been delivered, the actual span response of that analyzer 43, 44 or 45 is compared with the appropriate predetermined response curve stored in the computer until each analyzer has been checked.

The final calibration check is the mid-span check. In accordance with the invention, this check is run simultaneously for two or more of the analyzers 43, 44 and 45 sharing the same manifold 38. The number of analyzers that can be checked simultaneously is limited only by the mid-span concentration desired and the flow rates of the various gases. Using the apparatus shown in FIG. 1 and with the solenoid valves 24, 25 and 26 opened, the span gas for each analyzer 43, 44 and 45 is introduced at the same time through its respective inlet 14, 15 and 16 and into its corresponding inlet gas line 19, 20 and 21. At the same time, $N_2$ or air is also introduced into the gas divider 11 through inlet 13 and into inlet line 18. When the air or $N_2$ which is introduced into inlet line 18 is used as a separate diluent gas to be mixed with the span gases, the solenoid valve 23 is in the opened position. When no separate diluent gas is mixed with the span gases, air or $N_2$ is still introduced into inlet line 18 but the solenoid valve 23 remains closed.

The differential pressure regulators 31, 32 and 33 are designed to control the gas pressures at the inlets to capillaries 28, 29 and 30 so as to be equal to the gas pressure at the inlet to capillary 27 at all times. Each of the differential pressure regulators 31, 32 and 33 is responsive to a fluid signal, i.e., a pressure signal. As shown in FIG. 1, each of the pressure regulators 31, 32 and 33 is connected in parallel by means of a gas line 58 to the inlet gas line 18 for $N_2$ or air. Thus, when $N_2$ or air is supplied to the gas divider 11 through the inlet 13, a portion of the gas flows into the gas line 58 to provide a pressure signal for the individual pressure regulators 31, 32 and 33. The regulators 31, 32 and 33 are automatically adjusted based on the pressure signal. The flow rate of a particular gas is determined in part by the absolute pressure of the gas at the inlet to the capillary, the dimensions of the capillary, and the pressure drop across the capillary. This manner of control ensures that the ratios of the flow rates in the capillaries 28, 29 and 30 are in the same relationship to each other even though the pressure at the inlet to capillary 27 may change.

As an example, when the diluent gas is introduced into the gas divider 11 at twenty pounds per square inch and the span gases at thirty pounds per square inch, the differential pressure regulators 31, 32 and 33 will drop the pressure of each of the span gases to twenty pounds per square inch. It should be noted that the pressure signal on line 58 needs to be present, to allow regulators 31, 32 and 33 to provide span gases under pressure, even though solenoid valve 23 is closed to prevent the air or $N_2$ from mixing with the span gases.

The length and bore diameter of capillaries 28, 29 and 30, as well as 27 if a diluent gas is mixed with the span gases, are used to control the individual flow rates of the gases. The gases are then blended or mixed in the gas conduit 34 to generate the mid-span gas for the analyzers. After the gases enter this conduit 34 and are mixed, the resulting mid-span gas is delivered through the gas outlet line 35 and outlet 36 to the gas conduit 37 which is in communication with the outlet 36. From gas conduit 37, the generated mid-span gas is delivered to conduit 38 which, in turn, distributes the mid-span gas to the gas lines 39, 41 and 42. The pressure of the mid-span gas in each of these lines 39, 41 and 42 is further individually controlled by means of the spring loaded pressure regulators 46, 47 and 48. The pressure regulators 46, 47 and 48 vent to the atmosphere to insure that the pressure at the outlet of each of the regulators 46, 47 and 48 is maintained constant. Under normal operating conditions, this pressure is approximately three pounds per square inch. The needle valves 51, 52 and 53 may be used to individually control the flow rate of the mid-span gas through each of the lines 39, 41 and 42 and an indication of those individual flow rates is provided by the flow meters 54, 55 and 56.

The operation of the gas divider 11 to generate a mid-span gas comprising approximately 25% of each of the span gases (HC, $NO_2$, $CO_2$) and 25% diluent gas will now be described. To do this, capillaries 27, 28, 29 and 30 of the same length and bore diameter are used to generate approximately equal flow rates in each of those capillaries. The flow rate in each of the capillaries 27, 28, 29 and 30 is determined by the flow characteristics of the gas and the pressures on the inlet and outlet sides of the capillaries 27, 28, 29 and 30. Thus, when the inlet and outlet pressures of the capillaries 27, 28, 29 and 30 are maintained constant, the flow rate in each of those capillaries is determined by the flow characteristics of the gas.

Solenoid valve 22 is closed and solenoid valves 23, 24, 25 and 26 are opened. A diluent gas, i.e., either $N_2$ or air, is supplied to its inlet 13 and into its inlet gas line 18. At the same time, HC gas, $NO_2$ gas and $CO_2$ span gases are simultaneously supplied to their respective inlets 14, 15 and 16 and into their respective inlet gas lines 19, 20 and 21. The pressure of the diluent gas is used to maintain and control the pressure of each of the span gases by means of the pressure signal which is sent through line 58 and which is indicative of the pressure of the diluent gas. Each of the differential pressure controllers 31, 32 and 33 establishes and maintains the pressure of its span gases at the inlet to its corresponding capillary equal to the gas pressure at the inlet to capillary 27.

Because the capillaries 27, 28, 29 and 30 are of the same length and bore diameter and the flow characteristics of the gases are very similar, the flow rates through the capillaries will be approximately equal. As a result, the resulting mid-span gas which is generated and delivered through the outlet 36 will have approximately 25% of each of the HC, $NO_2$ and $CO_2$ span gas concentrations.

Other variations are also possible by changing the length and diameter of one or more of the capillaries 27, 28, 29 or 30. For example, a mid-span gas having approximately 20% of each of the HC, $NO_X$, and (CO or $CO_2$) span gas concentrations can be generated by making capillary 27 with appropriate dimensions compared to the other capillaries 28, 29 and 30 so that the flow rate of the diluent gas is twice that of each of the span gases.

As previously noted, the gas divider 11 may also be used to generate a mid-span gas for each of the analyzers 43, 44 and 45 simultaneously without mixing a separate diluent gas. To do this, solenoid valves 22 and 23 are closed and solenoid valves 24, 25 and 26 are opened. A diluent gas, HC gas, $NO_X$ gas, and CO or $CO_2$ gas are simultaneously supplied to their respective inlets 13, 14, 15 and 16 and into their respective inlet gas lines 18, 19, 20 and 21. In response to the pressure signal on line 58, the differential pressure regulators 31, 32 and 33 establish and maintain the pressure of their respective span gases at the inlet to the corresponding capillary equal to the pressure of the diluent gas at the inlet of capillary 27. This would result in a mid-span gas having approximately 33⅓% of the HC span gas concentration, 33⅓% of the $NO_X$ span gas concentration, and 33⅓% of the CO or $CO_2$ span gas concentration. Other concentrations are possible by changing the length and diameter of one or more of the capillaries 28, 29 or 30. For example, a mid-span gas having an approximate concentration of 50% HC, 25% $NO_X$ and 25% CO or $CO_2$ can be generated by making capillary 28 with appropriate dimensions compared to capillaries 29 and 30.

As previously noted, the inlet 12 and corresponding inlet gas line 17 can be used to purge the system before and/or after use. Solenoid valve 22 is opened for this purpose and air is then introduced into the gas divider 11 through inlet 12.

Figure 2:
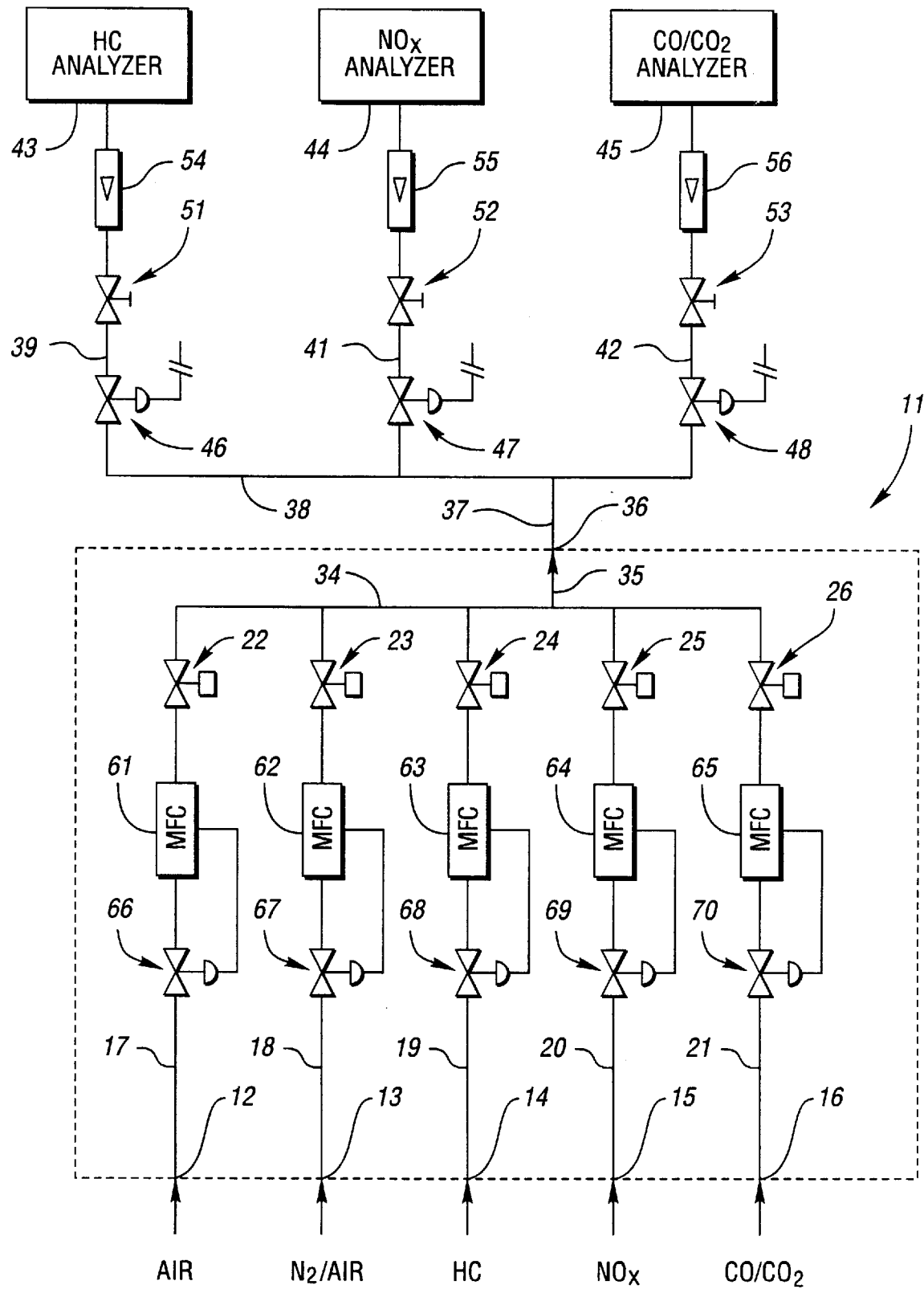
FIG. 2 is a schematic illustration of a gas dividing and blending system constructed in accordance with embodiments of the invention showing a gas divider connected to a plurality of gas analyzers for generating a mid-span gas to be used by each of these analyzers in running its mid-span check simultaneously.

FIG. 2 schematically illustrates an alternative gas dividing and blending system. The system of FIG. 2 is generally similar to that described in connection with the embodiments of FIG. 1. For that reason, components of this system in FIG. 2 which are the same as components of the FIG. 1 system are identified by the same reference numerals and will not be described again, except insofar as is necessary to understand the construction and operation of the embodiment of FIG. 2.

In the system of FIG. 2, a mass flow controller 61, 62, 63, 64, and 65 is coupled to each inlet line 17, 18, 19, 20, and 21 respectively. Each of the mass flow controllers 61, 62, 63, 64, and 65 operate in conjunction with a control valve 66, 67, 68, 69, and 70 respectively, each of which is also coupled to the corresponding inlet line. With this arrangement, each of the mass flow controllers 61 through 65 is programmed with a preset flow rate. Each of the flow controllers 61 through 65 measures the flow rate of gas through its respective inlet line 17 through 21 respectively and provides an electrical feedback signal to its corresponding control valve 66 through 70 respectively for maintaining the constant preset flow rate. Thus, by changing the flow rates of the various gases, different mid-span gases can be generated. With this arrangement, if air or $N_2$ is not used as a separate diluent gas to be mixed with the span gases, no gas need be introduced into lines 17 or 18.

By generating the mid-span gases from the required span gases for more than one analyzer simultaneously, additional separate mid-span gases are not required and all of the analyzers are allowed to run the mid-span calibration check at the same time. This results in a significant reduction in cost, as well as storage and plumbing requirements of the mid-span gases.

It should be readily apparent from the foregoing description that improved, cost effective and compact gas blending systems which generate mid-span gases have been illustrated and described. A mid-span gas may be generated for a plurality of analyzers at the same time so that the analyzers may have their mid-span gas calibration check performed at the same time. Although embodiments have been illustrated and described, various changes and modifications may be made without departing from the spirit and scope of the invention, as defined by the appended claims.

I claim:

1. A system for blending gases and for checking the calibration for each of at least a first analyzer for analyzing a first gas and a second analyzer for analyzing a second gas using the blended gases, said system comprising:

a source of a first span gas;

a source of a second span gas;

a plurality of span gas inlets each adapted to receive a respective one of said first and second span gases;

a plurality of span gas inlet lines each in communication with a respective one of said plurality of span gas inlets;

a plurality of flow controllers each coupled to a respective one of said plurality of span gas inlet lines for controlling the flow of a respective span gas supplied thereto;

a gas conduit for blending said first and second span gases from each of said span gas inlet lines to generate a mid-span gas having predetermined proportions of said first and second span gases determined in accordance with the relative flow rates of said first and second span gases through said plurality of span gas inlet lines such that said mid-span gas can be generated without blending a separate diluent gas;

means for simultaneously supplying said mid-span gas to each of the at least first and second analyzers; and means for simultaneously checking the calibration of each of the at least first and second analyzers.

2. A system as recited in claim 1, further comprising a dilution gas inlet adapted to receive a dilution gas and a dilution gas inlet line in communication with said dilution gas inlet.

3. A system as recited in claim 2, further comprising a flow controller in communication with said dilution gas inlet line for controlling the flow of dilution gas supplied thereto.

4. A system as recited in claim 3, further comprising a gas line in communication with said dilution gas inlet line and said span gas inlet lines for supplying a pressure signal to each of said flow controllers.

5. A system as recited in claim 3, wherein each of said flow controllers comprises a differential pressure controller and a capillary.

6. A system as recited in claim 5, further comprising a gas line in communication with said dilution gas inlet line and each of said differential pressure controllers.

7. A method of blending gases for generating a single mid-span gas usable for each of at least a first analyzer for analyzing a first gas and a second analyzer for analyzing a second gas, the method simultaneously using the mid-span gas for the analyzers, the method comprising the steps of:

providing at least a first and second span gas;

supplying at least said first and second span gases to a gas blender;

controlling the flow of each of said first and second span gases;

blending said first and second span gases to generate a mid-span gas having predetermined proportions of said first and second span gases; and supplying the mid-span gas to each of said plurality of analyzers simultaneously for checking calibration of at least the first and second analyzers.

8. A method as recited in claim 7, wherein said blending step further comprises blending a diluent gas with said at least two span gases to generate the mid-span gas.

9. A method for checking calibration of a plurality of gas analyzers, the method comprising the steps of:

zeroing each analyzer with a gas;

delivering a first gas into a first one of the gas analyzers to run an actual span check on said first analyzer;

delivering a second gas into a second one of the gas analyzers to run an actual span check on said second analyzer;

comparing said actual span check on said first analyzer with a predetermined response curve for said first analyzer;

comparing said actual span check on said second analyzer with a predetermined response curve for said second analyzer;

introducing said first span gas and said second span gas into a manifold;

blending said first span gas and said second span gas in said manifold to create a mid-span gas;

delivering said mid-span gas simultaneously to said first and second analyzers to run a mid-span check on said first and second analyzers;

comparing said mid-span check on said first analyzer with a predetermined response curve for said first analyzer; and comparing said mid-span check on said second analyzer with a predetermined response curve for said second analyzer.

10. The method of claim 9, wherein said mid-span gas has a concentration of less than 100%.

11. The method of claim 9, wherein said blending step further comprises blending a diluent gas with said first and second span gases to generate said mid-span gas.

12. The method of claim 9, including the step of using said mid-span gas to produce an actual response curve.

13. The method of claim 9, including the step of producing an actual response curve including an actual zero response, an actual mid-span response and an actual span response.

14. The method of calibrating of claim 9, including the step of running a mid-span calibration check on all of the analyzers simultaneously.

15. The method of calibrating of claim 9, including the step of introducing equal concentrations of said first and second gases.

16. The method of calibrating of claim 9, including the step of introducing unequal concentrations of said first and second gases.

* * * * *